(12) United States Patent
Iott et al.

(10) Patent No.: US 10,028,775 B2
(45) Date of Patent: *Jul. 24, 2018

(54) DEVICES AND METHODS FOR INSERTING A VERTEBRAL FIXATION MEMBER

(71) Applicant: GLOBUS MEDICAL, INC., Audubon, PA (US)

(72) Inventors: Andrew Iott, Newtown Square, PA (US); Edward Karpowicz, Sewell, NJ (US); Douglas Cahill, Lititz, PA (US); Robert Rightler, Pennsburg, PA (US)

(73) Assignee: Globus Medical, Inc., Audubon, PA (US)

( * ) Notice: Subject to any disclaimer, the term of this patent is extended or adjusted under 35 U.S.C. 154(b) by 75 days.

This patent is subject to a terminal disclaimer.

(21) Appl. No.: 15/291,533

(22) Filed: Oct. 12, 2016

(65) Prior Publication Data
US 2017/0027623 A1 Feb. 2, 2017

Related U.S. Application Data

(63) Continuation of application No. 14/526,707, filed on Oct. 29, 2014, now Pat. No. 9,486,255, which is a continuation of application No. 12/413,058, filed on Mar. 27, 2009, now Pat. No. 8,900,238.

(51) Int. Cl.
*A61B 17/70* (2006.01)
*A61B 17/02* (2006.01)

(52) U.S. Cl.
CPC ...... *A61B 17/7085* (2013.01); *A61B 17/0206* (2013.01); *A61B 17/7004* (2013.01); *A61B 17/708* (2013.01); *A61B 17/7077* (2013.01)

(58) Field of Classification Search
CPC ........ A61B 17/7083–17/7089; A61B 17/8861; A61B 17/8872
See application file for complete search history.

(56) References Cited

U.S. PATENT DOCUMENTS

| | | | |
|---|---|---|---|
| 6,245,072 B1 | 6/2001 | Zdeblick et al. | |
| 7,758,617 B2 | 7/2010 | Iott et al. | |
| 8,038,699 B2 | 10/2011 | Cohen et al. | |
| 2003/0208203 A1* | 11/2003 | Lim | A61B 17/7083 606/86 A |
| 2005/0090824 A1* | 4/2005 | Shluzas | A61B 17/7083 606/60 |
| 2008/0077138 A1 | 3/2008 | Cohen et al. | |
| 2008/0125788 A1* | 5/2008 | Cohen | A61B 17/7076 606/104 |
| 2009/0082811 A1 | 3/2009 | Stad et al. | |
| 2010/0331901 A1* | 12/2010 | Iott | A61B 17/701 606/86 A |
| 2017/0112631 A1* | 4/2017 | Kuyler | A61F 2/447 |
| 2018/0008324 A1* | 1/2018 | Cryder | A61B 17/7086 |

FOREIGN PATENT DOCUMENTS

WO 2007059207 A2 5/2007

* cited by examiner

*Primary Examiner* — Jacqueline Johanas (57) ABSTRACT

Devices, systems, and methods for inserting a vertebral stabilization member, such as a rod. The insertion device includes an outer guide tube, a pin assembly including a pin and a pusher member extending therethrough. The insertion device is configured to actuate a rod between a first orientation and a second orientation angled with respect to the first orientation in order to position the rod in an appropriate location for attachment to bone.

20 Claims, 13 Drawing Sheets

DEVICES AND METHODS FOR INSERTING A VERTEBRAL FIXATION MEMBER

CROSS REFERENCE TO RELATED APPLICATION

The present application is a continuation of U.S. patent application Ser. No. 14/526,707, file Oct. 29, 2014, which is a continuation of U.S. patent application Ser. No. 12/413,058, filed Mar. 27, 2009, now U.S. Pat. No. 8,900,238, the entire disclosures of which are incorporated herein by reference in their entireties for all purposes.

FIELD OF THE INVENTION

The present invention relates generally to devices and methods for inserting a vertebral fixation member, and more particularly, but not exclusively, to rod insertion devices and methods.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated by immobilizing a portion of the spine. This treatment typically involves affixing a plurality of screws and/or hooks to one or more vertebrae and connecting the screws or hooks to an elongate rod that generally extends in the direction of the axis of the spine.

Treatment for these spinal irregularities often involves using a system of pedicle screws and rods to attain stability between spinal segments. Instability in the spine can create stress and strain on neurological elements, such as the spinal cord and nerve roots. In order to correct this, implants of certain stiffness can be implanted to restore the correct alignment and portion of the vertebral bodies. In many cases, an anchoring member such as a pedicle screw along with a vertical solid member can help restore spinal elements to a pain free situation, or at least may help reduce pain or prevent further injury to the spine.

As the science and technology of spine surgery continues to progress, there is an increasing interest in developing alternative, minimally invasive, methods to conventional "open" spine surgery. The goals of these less invasive alternatives are to avoid the surgical exposure, dissection, and retraction of muscles and tissues that is necessary with "open" surgery. In general, a minimally invasive spine surgery system should be able to perform the same procedure as the traditional open technique, but through smaller incisions instead of one longer incision. As a result, some physicians feel that using a minimally invasive spine surgery system generally causes less soft tissue damage, reduces blood loss and reduces recovery time. In addition, patients generally prefer the smaller scars that are left using a minimally invasive approach.

Historically, spine fusion surgery including pedicle screw fixation with deep placement of rods has been one area that has presented significant challenges for minimally invasive approaches. However, advancement in technologies such as fluoroscopy and improvements in optics have contributed to the advent of a few minimally invasive spine fusion surgery techniques.

SUMMARY OF THE INVENTION

A device and method for inserting a vertebral stabilization member is disclosed. In one embodiment, the stabilization member is releasably clampable to an insertion device between first and second clamping members at a clamping location spaced from a midline of the stabilization member. The insertion device and stabilization member are deliverable through an access sleeve and the stabilization member is rotatably actuatable to position the stabilization member in relation to a bone anchor.

BRIEF DESCRIPTION OF THE DRAWINGS

The invention will be more readily understood with reference to the embodiments thereof illustrated in the attached drawing figures, in which.

Throughout the drawing figures, it should be understood that like numerals refer to like features and structures.

DETAILED DESCRIPTION

The various embodiments of the invention will now be described with reference to the attached drawing figures. The following detailed description of the invention is not intended to be illustrative of all embodiments. In describing the various embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose. The features of one embodiment may be employed with other embodiments as the skilled artisan would recognize, even if not explicitly stated herein.

Figure 1:
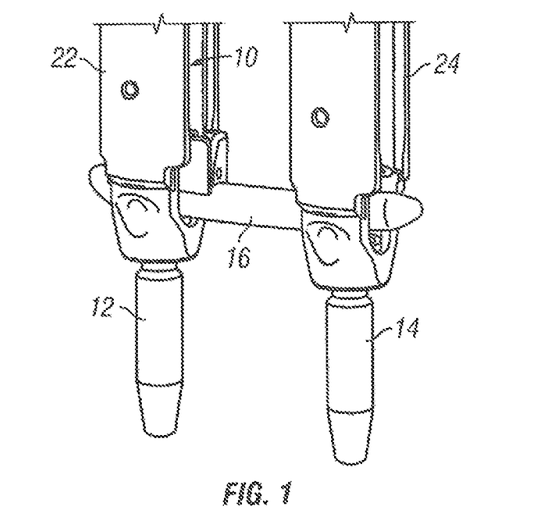
FIG. 1 is a perspective view of one embodiment of a stabilization member and insertion device shown during on embodiment of an installation method according to the present invention.
Figure 2:
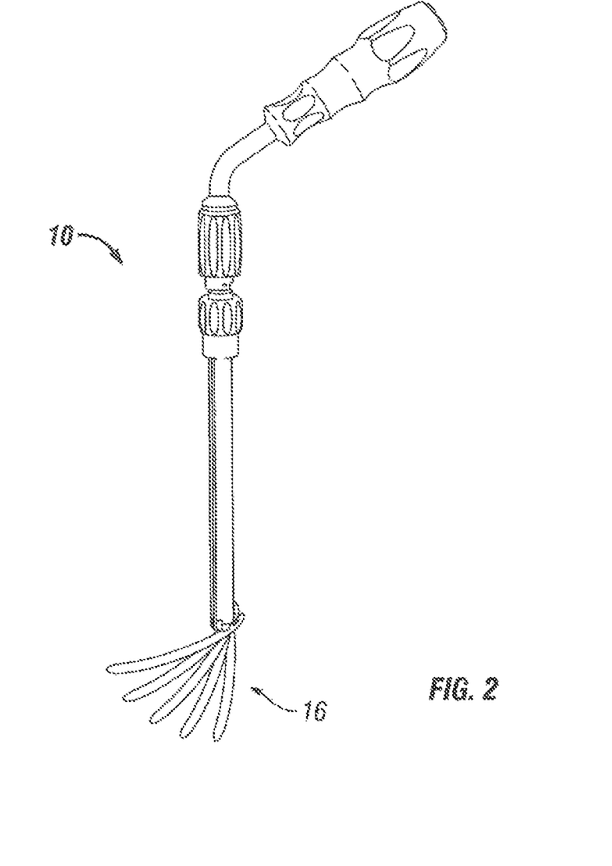
FIG. 2 is a perspective view of one embodiment of a stabilization member insertion device according to the present invention.

Referring to FIG. 1, one embodiment of a stabilization member insertion device 10 is shown positioned within one embodiment of a sleeve 22 that is mated to a first anchor 12. A second anchor 14 is shown attached to a second sleeve 24. A connecting member or stabilization member 16 is shown attached to device 10 and is configured to connect and/or extend between the first and second anchors 12, 14 for stabilizing at least a portion of a vertebrae of a patient. According to one variation, first anchor 12 may be positioned within a body of a patient through any known surgical methods, including but not limited to, through a first minimally invasive or percutaneous opening. Second anchor 14 is also positionable within a body of a patient through any known surgical methods, including but not limited to, through a second minimally invasive or percutaneous opening. In the alternative, first and second anchors 12, 14 may be inserted through an open, mini-open, or mixed open and minimally invasive procedure. In one embodiment, first and second anchors 12, 14 are configured to engage first and second vertebra.

Stabilization member 16 is positionable within the body of a patient through a first opening in the skin to engage and connect first and second anchors 12, 14. According to one embodiment, one of sleeves 22, 24 may extend from anchors 12, 14 and facilitate insertion of anchors 12, 14 into a vertebral body. Stabilization member 16 may be installed between anchors 12, 14 and clamping members, screw caps or set screws may be installed for fixation of stabilization member 16 to anchors 12, 14. Stabilization member 16 may be installed through any known surgical methods including, but not limited to minimally invasively, percutaneously or through an open procedure or non-percutaneously into receiving portions or channels 26 of anchors 12, 14. According to one embodiment, connecting member or stabilization member 16 generally comprises an elongate rod or shaft. Stabilization member 16 may have an arcuate or curvilinear shape. In alternative embodiments, however, stabilization member 16 can include any configuration known for a rod, implant, or fastener, and can be straight or have any curvature along its length including a compound curvature. As shown in FIG. 1, a stabilization member insertion device 10 may be inserted into sleeve 22 to facilitate insertion of stabilization member 16 into anchors 12, 14. Although a second sleeve 24 is depicted in FIG. 1 as being attached to anchor 14, a second sleeve 24 may or may not be connected to second anchor 14, depending on the preference of a surgeon user.

In one embodiment, stabilization member insertion device 10 is releasably and rotatably linked to the stabilization member 16 and the stabilization member insertion device 10 is configured and dimensioned to be received within a single sleeve 22, 24 such that the insertion device 10 and stabilization member 16 are moveable in the longitudinal direction within the sleeve to position stabilization member 16 adjacent the distal end thereof. As will be discussed in more detail below, stabilization member 16 is deliverable through the sleeve in a first orientation substantially parallel to the axis of the sleeve and is rotatable to a second orientation at an angle with respect to the first orientation. Furthermore, the stabilization member 16 is rotatably actuatable by insertion device 10 independent of movement along the axis of the sleeve, i.e. the stabilization member 16 may be rotated by insertion device 10 anywhere along the length of the sleeve. Such a feature may be particularly advantageous, for example, to adjust the pathway or route that the stabilization member 16 travels through the body tissue during installation. In this regard, those skilled in the art will appreciate that a virtually limitless number of different pathways that a stabilization member 16 may travel and this features provides great flexibility to a surgeon user. In addition, due to the independent aspect of the rotation of the stabilization member, rotation may be actuated or independently controlled without moving the insertion device with respect to sleeve 22. In this regard, rotation of stabilization member 16 may be rotated without downward exertion of force upon the sleeve and/or anchor.

Figure 3:
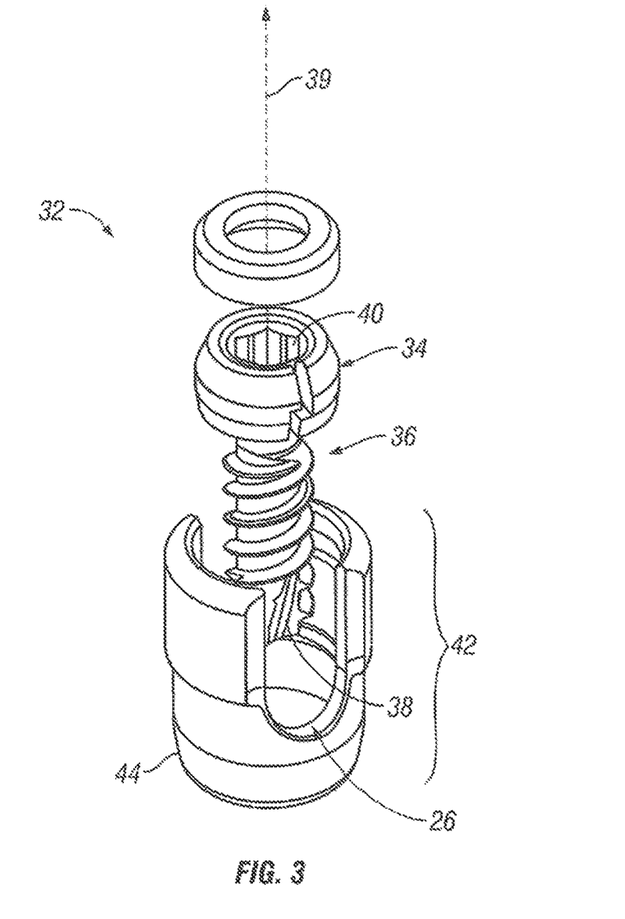
FIG. 3 is an exploded view of one embodiment of a screw.
Figure 4:
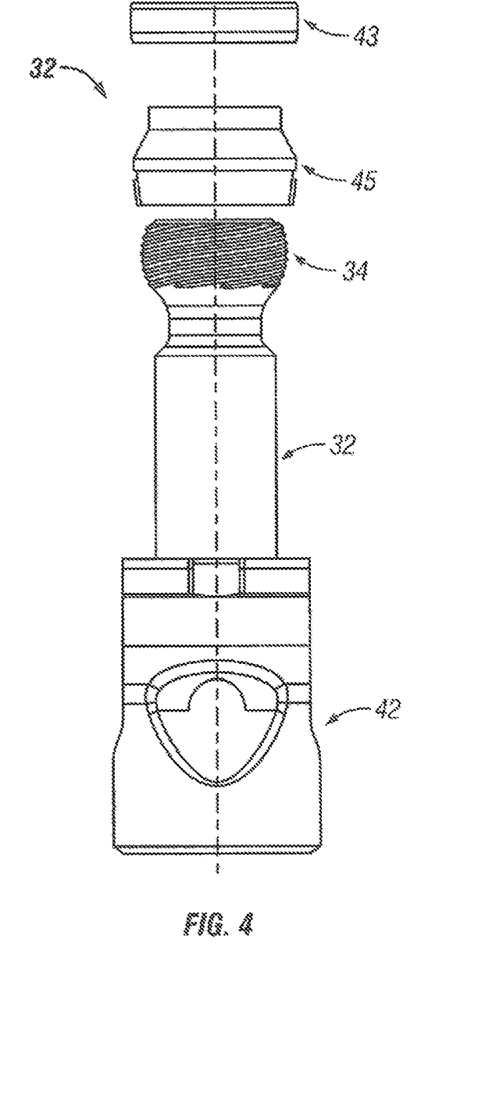
FIG. 4 is an exploded view of another embodiment of a screw.
Figure 5:
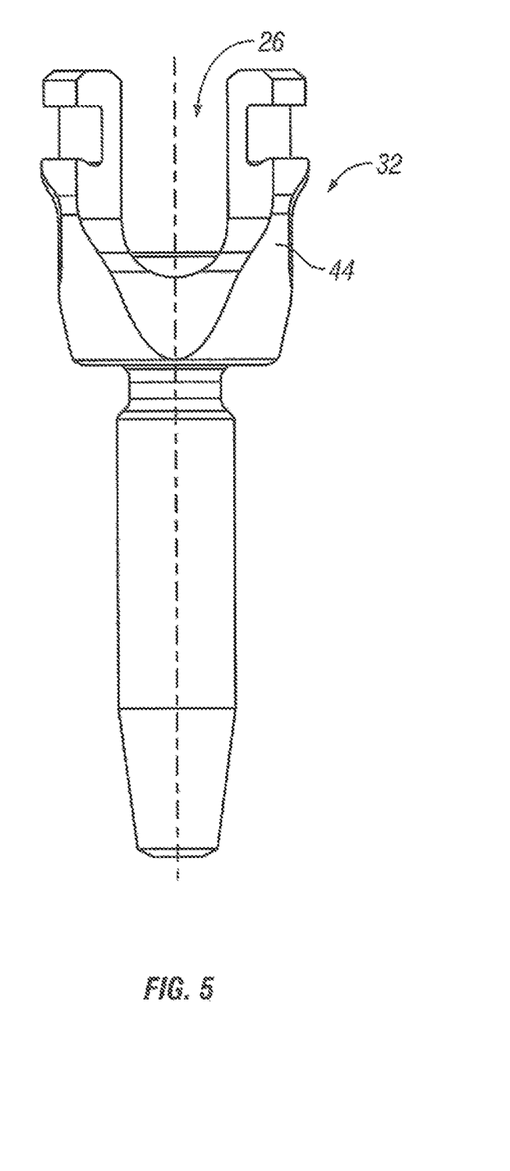
FIG. 5 is an assembly view of the embodiment of the screw of FIG. 4.

Referring now to FIGS. 3-5, exemplary embodiments of anchors that may be utilized with the invention are shown. Referring to FIG. 3, one embodiment of an anchor 32 is shown and generally comprises a bone fastener such as a bone screw 32 with a head 34 and a shaft or shank 36 having bone engaging threads. As shown in FIG. 3, screw 32 is cannulated with a central passage or lumen 38 extending along a central axis 39, however, non-cannulated screws may also be used. Head 34 includes a tool engagement surface or opening 40 configured to receive a driving tool to provide torque and drive the screw into bone. In one embodiment, screw 32 is a polyaxial screw assembly that has a coupling element 42 pivotably coupled to, head 34 of screw 32. A wedge 43 and clamp assembly 45 may be housed within coupling element 42 to facilitate locking the screw 32 with respect to coupling element 42. In this regard, screw 32 is capable of rotating within coupling element 42 to selectably assume a plurality of angles. Referring to FIGS. 4-5, another exemplary embodiment of a bone screw 32 is shown. Still another example of a polyaxial screw that may be used with the present invention is described in U.S. Pat. No. 7,503,924, the entire contents of which are incorporated by reference.

Referring to the embodiments of FIGS. 3-5, coupling element 42 is configured and adapted to receive the stabilization member 16. In general, coupling element 42 includes a U-shaped body 44 defining a channel 26 in which stabilization member 16 may be locked or fixed in place by, for example, a locking cap. In alternate embodiments, alternative means of rigidly coupling stabilization member 16 to an anchor may be used by those skilled in the art, including alternative configurations of coupling elements and locking devices or methods. In one embodiment, coupling element 42 includes features to couple with sleeves 22, 24.

Figure 6:
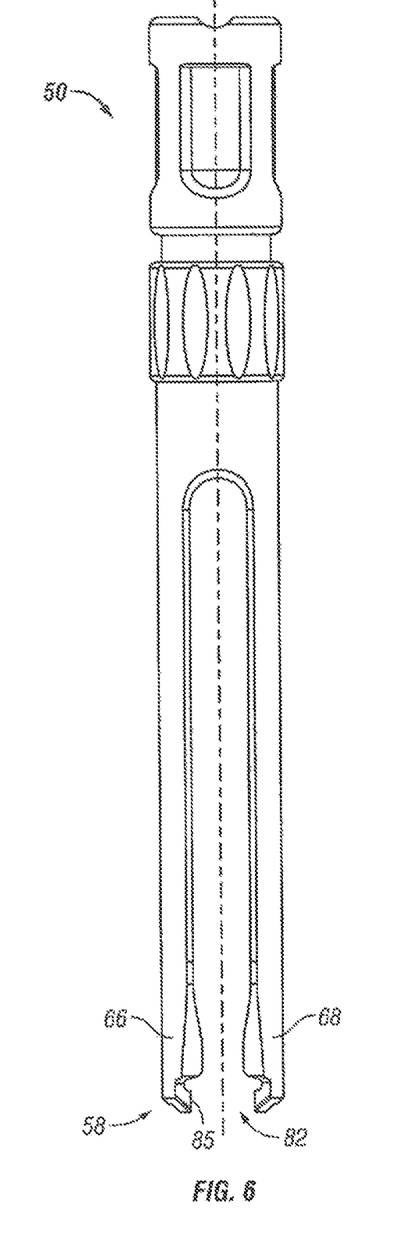
FIGS. 6-7 are side and front views of one embodiment of an access sleeve.
Figure 7:
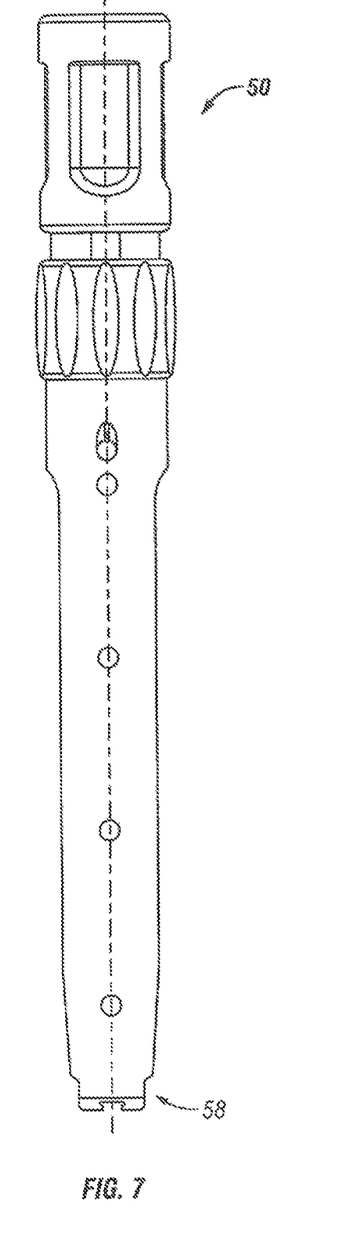

In the illustrated embodiment, a sleeve may extend from the anchors 12, 14 and provide a portal or passageway through the body of a patient to access anchors 12, 14. Referring to FIGS. 6-7, one embodiment of a sleeve 50 according to the invention is shown comprising cannula 54 extending from a proximal end 56 to a distal end 58 along an axis 60. A central channel 62 extends axially through sleeve 50. In this regard, cannula 54 generally comprises an extended tube with a generally cylindrical top portion 64 and a pair of generally rigid arms 66, 68 extending axially from top portion 64 in a distal direction. Slots or openings 76 extend along the lateral sides of sleeve 50 to provide access to central channel 62 of sleeve 50. Sleeve 50 may be made of any material suitable for surgical instruments. In one preferred embodiment, sleeve 50 may be made of a metallic material.

In operation, arms 66, 68 of sleeve 50 may include a retainer portion 82 at its distal end to attach an anchor to the distal end of sleeve 50. In this regard, arms 66, 68 may include projections 84 extending laterally inward from the distal end to engage a corresponding feature on the anchor to provide additional retention capability.

When sleeve 50 is assembled to an anchor, as shown in FIG. 1, coupling element 42 of bone screw 32 is received within retainer portion 82 at a distal end 58 of sleeve 50. In this regard, retainer portion 82 may snappably or resiliently receive the coupling element 42 of screw 32. The inner wall 85 of retainer portion 82 is shaped to conform to the outer perimeter of coupling element 42 such that when arms 66, 68 engage an anchor, the coupling element 42 of screw 32 is rotationally and axially fixed with respect to sleeve 50 or radially contained within sleeve 50

Figure 8:
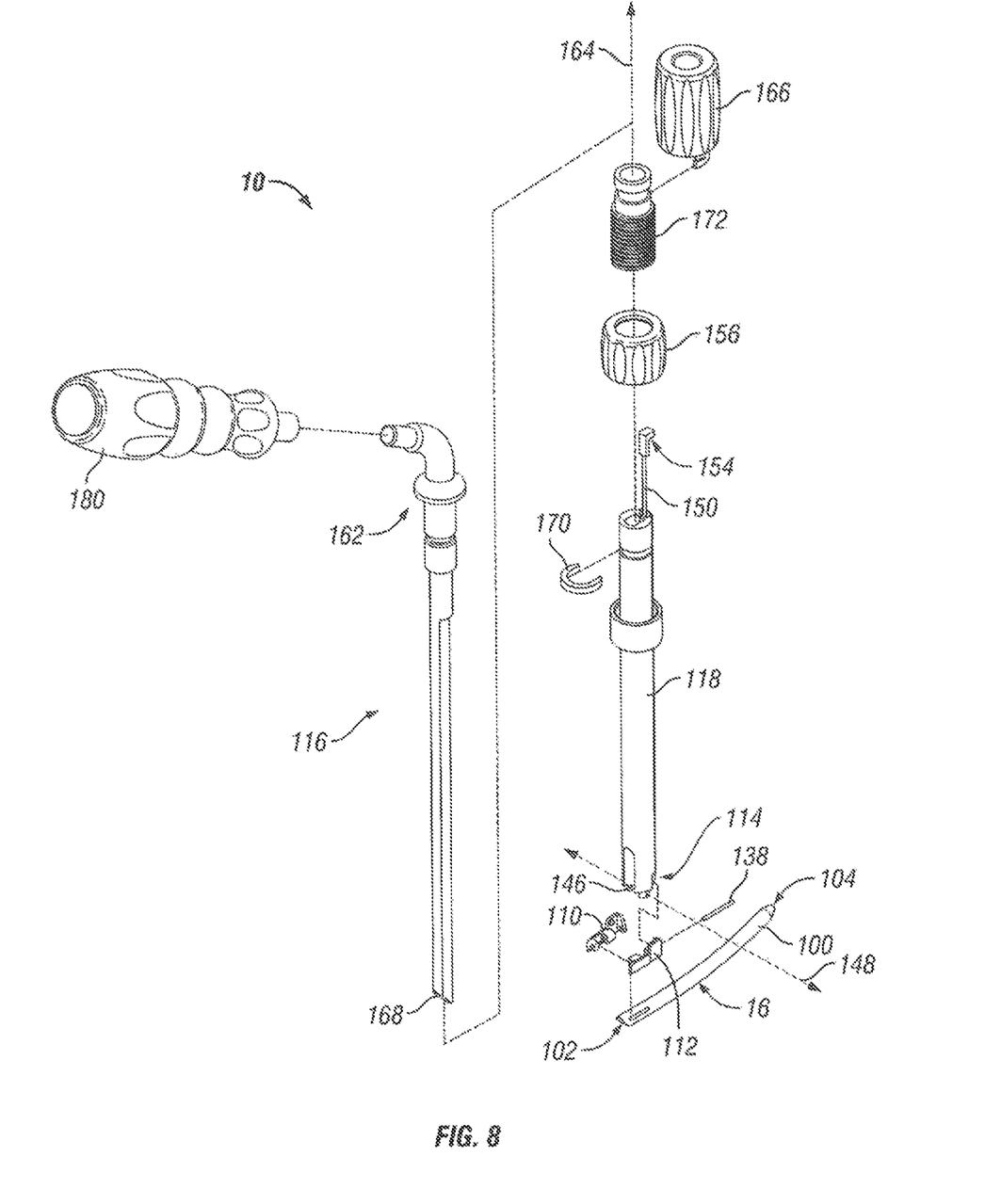
FIG. 8 is an exploded view of one embodiment of the insertion device of FIG. 2.
Figure 9:
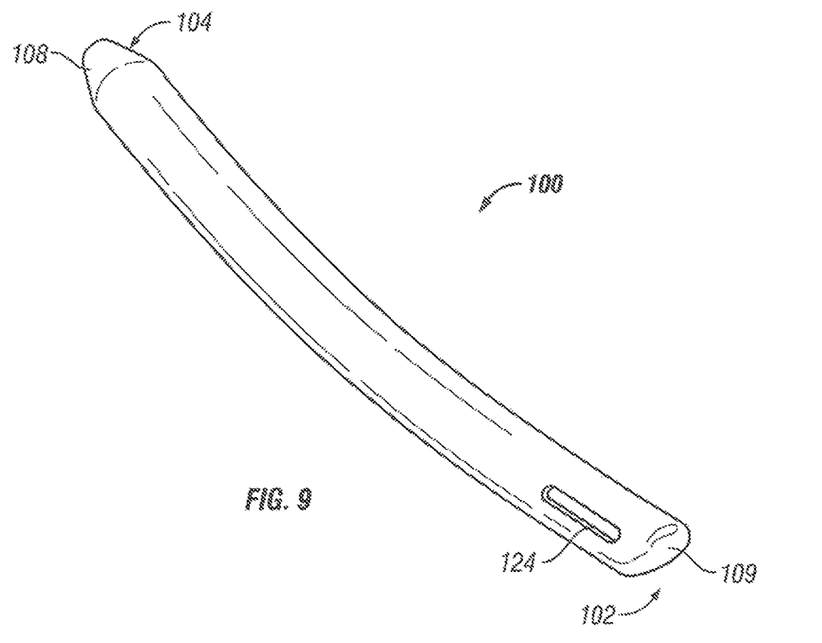
FIG. 9 is a perspective view of one embodiment of a stabilization member according to the present invention.
Figure 10:
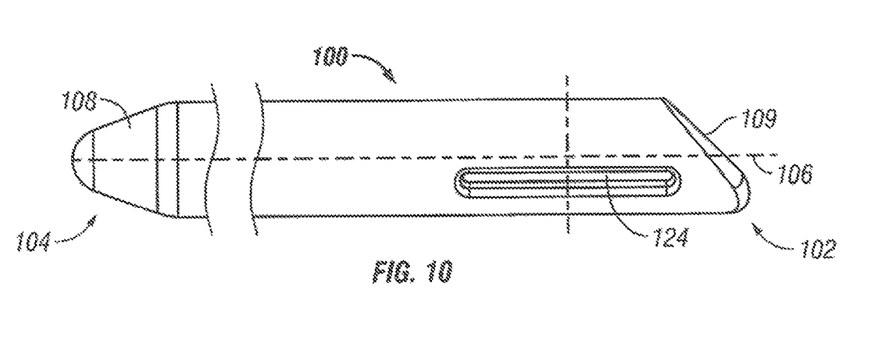
FIGS. 10-11 are enlarged side and top views of the stabilization member of FIG. 9.
Figure 11:
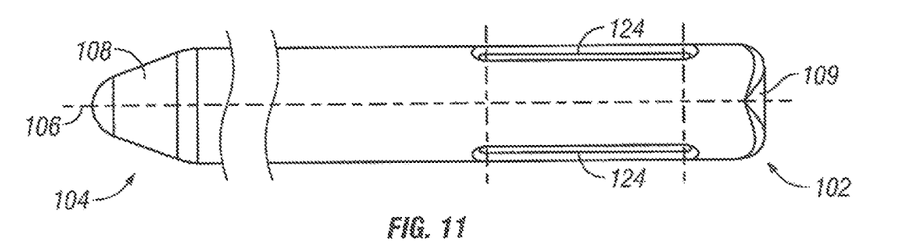

Referring now to FIGS. 8-11, one embodiment of a stabilization member 16 and insertion device 10 is shown. As shown in FIGS. 9-11, stabilization member 16 generally comprises an elongate rod 100 extending from a proximal end 102 to a distal end 104 along an axis 106. In one embodiment, rod 100 is curved or arcuate along its length. However, in alternate embodiments, rod 100 may have any alternate shape. According to one aspect of the embodiment, rod 100 includes a generally tapered or conical shaped nose or tip 108 at its distal end 104 to facilitate insertion and installation of rod 100 into the body of a patient. In alternate embodiments, tip 108 may have varied shapes and sizes. Proximal end 102 of rod 100 comprises a generally concave or rounded ramped tip surface 109 angled with respect to longitudinal axis 106 configured and dimensioned to interface or engage with actuating or pushing member 116 of insertion device 10.

Referring to FIG. 8, insertion device 10 generally comprises a means for clamping to or holding stabilization member 16 and means for controllably actuating or rotating the stabilization member 16 about the distal end of the device. According to one variation, insertion device 10 is an assembly generally comprising a pair of clamp members 110, 112 pivotably attached adjacent a distal end 114 that may be selectably actuatable to clamp, fix or hold the stabilization member 16 adjacent the distal end thereof. Insertion device 10 additionally comprises a drive shaft or actuatable pusher assembly 116 extendable centrally within an outer guide tube 118 and linearly advanceable with respect thereto to facilitate the rotation or pivoting of the stabilization member 16 with respect to guide tube 118.

Referring again to FIGS. 9-11, in one embodiment, rod 100 may include a pair of diametrically opposed indentations 124 spaced from proximal end 102 of rod 100. In one variation, indentations 124 are generally elongate grooves extending generally parallel with axis 106. Indentations 124 are configured and dimensioned to releasably rotatably engage clamp members 110, 112 of insertion device 10 such that rod 100 may pivot with respect to distal end 114. To attach rod 100 to clamp members 110, 112, clamp members may be separatable to engage or snap into indentations 124. In operation, once ridges cooperatively engage indentations 124, rod 100 may rotate or pivot about distal end 114.

One embodiment of a means for clamping comprises a left clamp member 110 and a right clamp member 112 pivotably attached to a distal end of guide tube 118. A pair of openings 146 are provided adjacent the distal end of guide tube 118 and receives clamp members 110, 112 therein to releasably clamp to rod 100 such that rod 100 may rotate thereabout.

Figure 12:
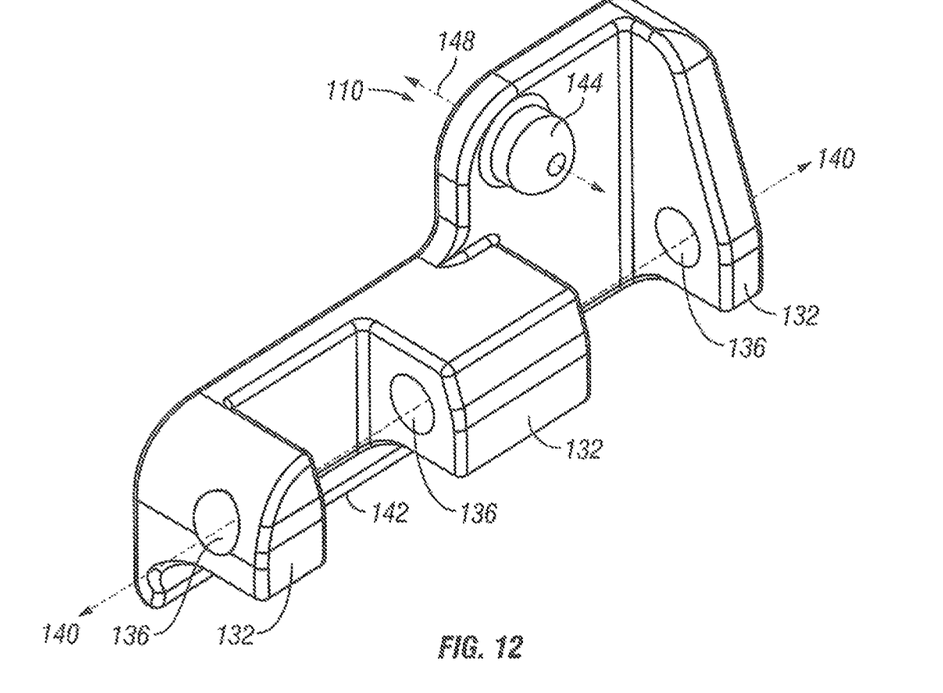
FIGS. 12-13 are perspective views of left and right clamp members, respectively.
Figure 13:
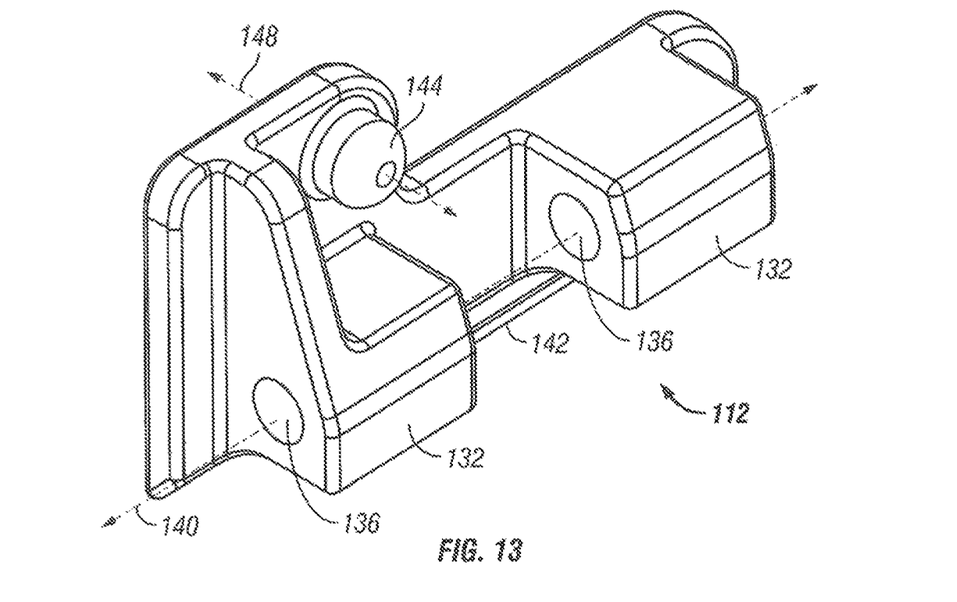

Referring to FIGS. 12 and 13, finger or flange portions 132 extend laterally inward from clamp member sidewalls 134 and define a hole 136 extending longitudinally therethrough. Clamp members 110, 112 may be assembled with flange portions 132 overlapping laterally and with holes 136 aligned to receive a pin 138 and defining a pivot axis 140. In this regard, the left and right clamp members 110, 112 may pivot with respect to each other about pin 138 and axis 140. A clamp ridge 142 may be defined along a portion of the lower edge of each clamp member 110, 112 such that when clamp members 110, 112 pivot about axis 142, ridges 142 may move towards and away from each other to hold, clamp, or fix rod 100 therebetween. According to one variation, rod 100 may be clamped or held about the upper portion thereof and with clamp members 110, 112 within the profile of rod 100 such that no portion of clamp members 110, 112 extend or protrude beyond the radius of rod 100. In one embodiment, rod 100 is generally cylindrical with a generally circular cross section and clamp members 110, 112 engage rod 100 on an upper portion of the rod spaced from the midline or diameter of the rod. In this regard, when clamp members 110, 112 are in a clamping position to clamp or hold rod 100, they are generally spaced apart a distance less than the diameter of the rod. It may be appreciated that as a result of such a design, rod 100 may be loaded directly into an anchor receiver member at the rod clamping location without requiring additional space or room to allow the clamp members to enter therein. Those skilled in the art may appreciate that such a feature may be advantageous in facilitating the use of legacy anchors or screws without the requirement that receiver portions be especially sized and dimensioned and/or retrofitted to accommodate clamp members 110, 112.

Figure 14:
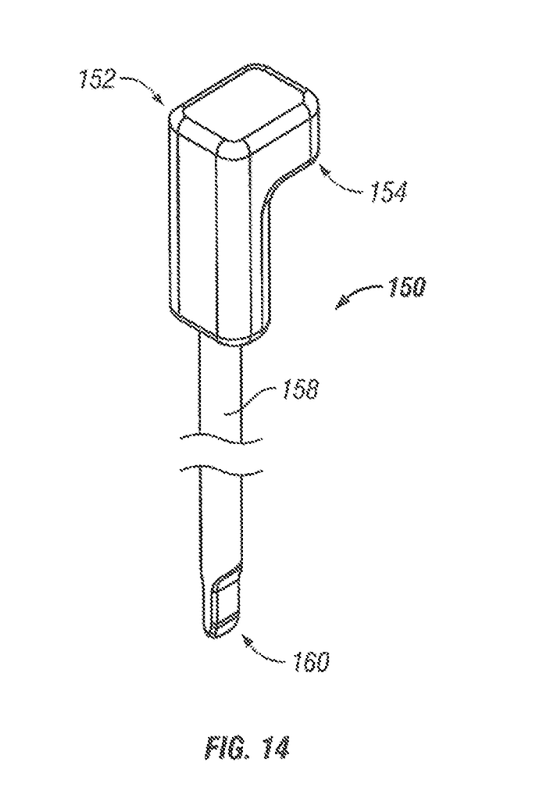
FIG. 14 is a perspective view of a longitudinal pin assembly.
Figure 15:
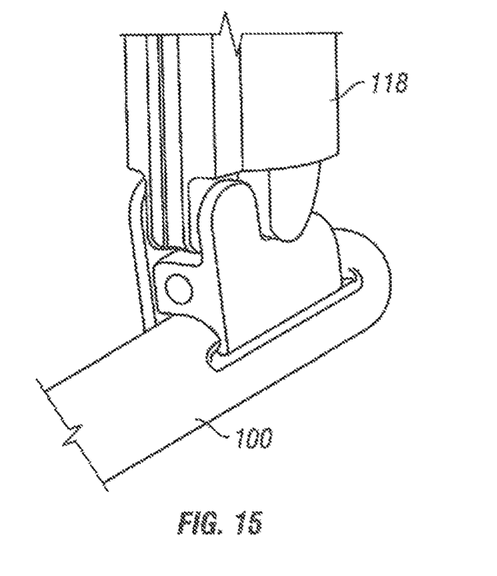
FIG. 15 is an enlarged partial perspective view of the insertion device of FIG. 2 shown in a first position.
Figure 16:
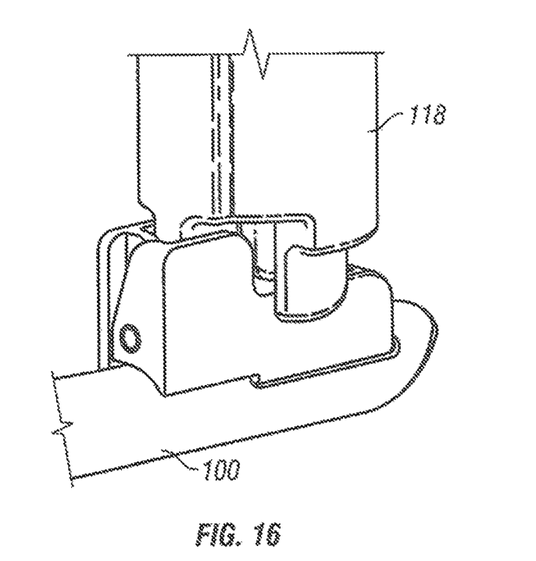
FIG. 16 is an enlarged partial perspective view of the insertion device of FIG. 2 shown in a second position.
Figure 17:
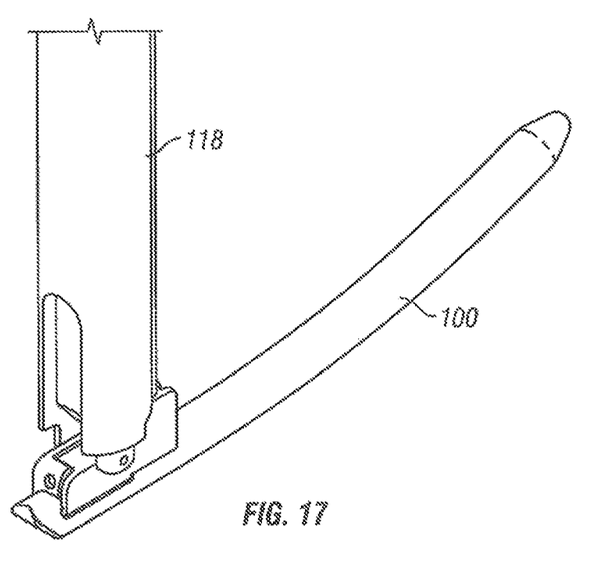
FIG. 17-18 are side and rear partial perspective views of the insertion device of FIG. 2 shown in the second position.
Figure 18:
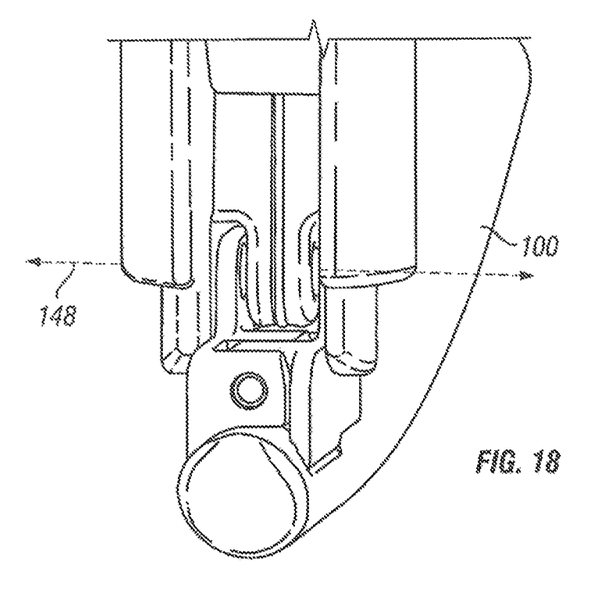

Clamp members 110, 112 may be pivoted about axis 140 or actuated to clamp rod 100 remote from the distal end 114 via pin assembly 150 that extends through guide tube 118. Referring to FIG. 14, in one variation a proximal end 152 of the pin assembly has a block or finger portion 154. As shown in FIG. 8, finger portion 154 is configured to engage an interior of thumb nut 156 such that as the thumb nut is rotated, the pin assembly 150 may be linearly advanced or retracted as desired by a user. Thumb nut 156 is internally threaded and threadably engages collar 172. In this regard, threaded collar 172 may be axially constrained to guide tube 118 via C-clip 170. In alternate embodiments, threaded collar 172 may be integrally formed with guide tube 118 such as via welding.

Figure 19:
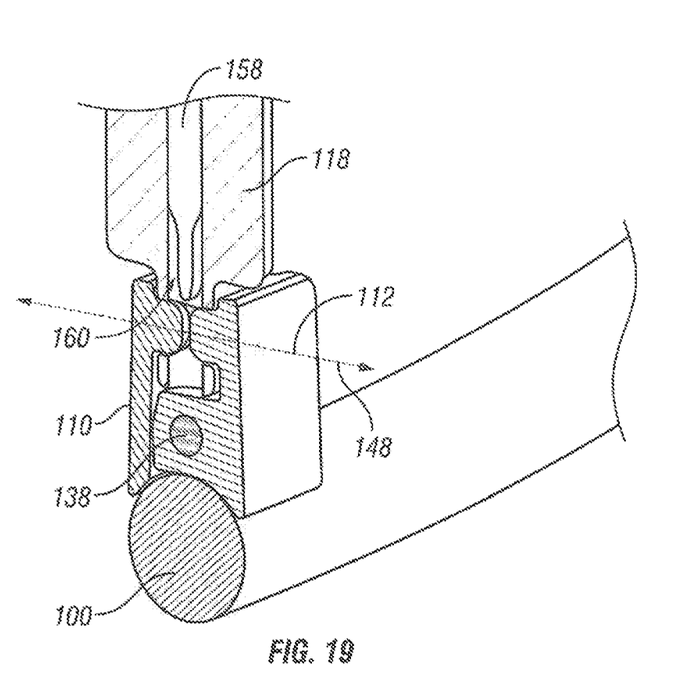
FIG. 19 is a partial cross-sectional view of the insertion device of FIG. 2, shown with the clamp assembly unclamped to the stabilization member.
Figure 20:
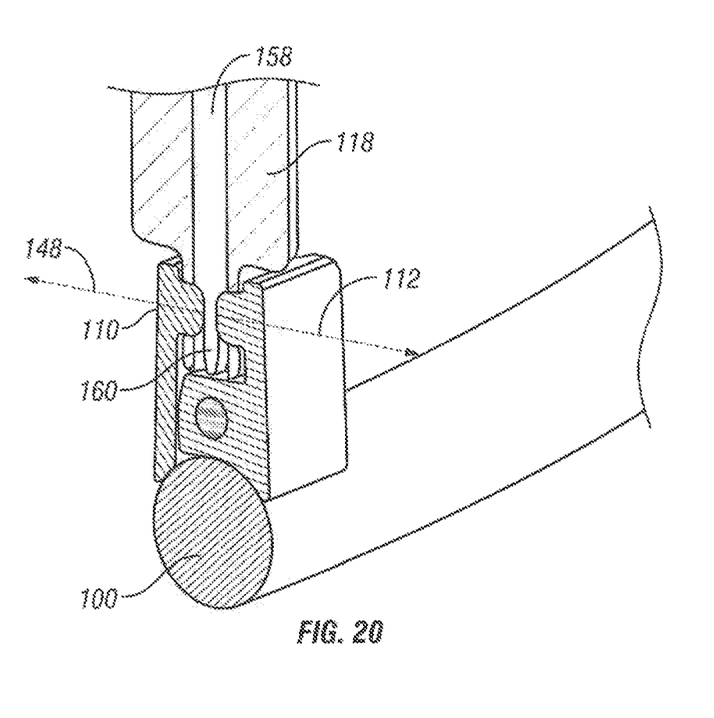
FIG. 20 is a partial cross-sectional view of the insertion device of FIG. 2, shown with the clamp assembly clamped to the stabilization member.

As best seen in FIGS. 19-20, pin assembly 150 is axially moveable within guide tube 118 and the distal end of pin 158 is configured to engage clamp members 110, 112 to cause the clamp members to pivot about axis 140. In a first position, shown in FIG. 19, the distal most tip 160 of pin 158 is spaced from the distal most end 114 of tube 118 and spaced distally from between protrusions 144 of clamp members 110, 112. In this position, clamp members 110, 112 may pivot apart such that rod 100 is not clamped therebetween. Referring to FIG. 20, pin assembly 150 may be advanced to a second position, shown in FIG. 20, with the distal most tip 160 of pin 158 advanced distally between protrusions 144. In this second or clamped position, the ridges 142 of clamp members 110, 112 may move towards each other to clamp or hold rod 100 therebetween.

A protrusion 144 extends inward from each clamp member sidewall, respectively. Protrusions 144 are generally cylindrical with rounded free ends configured and dimensioned to linkingly engage openings provided in the distal end of insertion device 10. Protrusions 144 are generally coaxially positionable within openings 146 and aligned along a pivot axis 148 defined through the center thereof. Pivot axis 148 extends generally perpendicular to a central axial plane of rod 100 and clamp pivot axis 140. In this regard, when assembled to device 10, clamp members 110, 112 are axially fixed and rotatable about the distal end thereof such that when rod 100 is clamped therebetween, rod 100 may pivot about axis 148 during installation in a patient.

One embodiment of a means for controllably actuating, pivoting, or rotating the stabilization member 16 about the distal end of insertion device 10 generally comprises a first member and a second member, wherein the first member is linearly translatable with respect to the second member along the longitudinal axis of the device and the stabilization member is linkingly engaged to the first member and rotatably engaged to the second member. When the first member is translated with respect to the second member along the longitudinal axis, the stabilization member rotates about the second member. According to one embodiment, shown in FIG. 8, stabilization member insertion device 10 generally comprises an outer guide tube 118 and a pusher assembly 116 concentrically disposable within screw extension or sleeve 50 to position a stabilization member 16 in relation to the attached screw(s).

As best seen in FIG. 8, pusher assembly 116 generally comprises a pusher member 160 integral to a threaded drive shaft or stein portion 162. Pusher assembly 116 is configured and dimensioned to fit within outer tube 118 such that it is moveable with respect to outer tube 118 along a longitudinal axis 164. A knob 166 is internally threaded to mate with external threads of drive shaft 162 Such that rotation of knob 166 causes linear translation of pusher assembly 116 with respect to outer guide tube 118 along axis 164. Pusher member 116 includes a distal end 168 configured and dimensioned to pushingly and/or slidingly engage proximal end 102 of rod 100.

Figure 24:
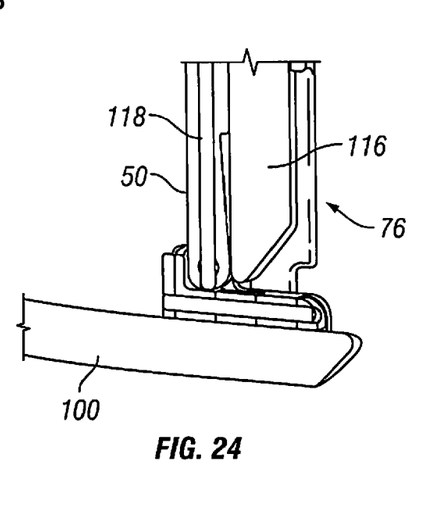

In operation, when knob 166 is rotated, drive shaft 116 is moved downward or in the distal direction along axis 164 and distal end 168 of pusher member 116 pushes or drives the proximal end 102 of rod 100 downward or in the distal direction and causes rod 100 to rotate or pivot about pivot axis 148. In this regard, referring to FIGS. 21-24, rod 100 is moveable from a generally upright orientation or position or a position wherein axis 106 is aligned with or parallel to axis 164 (FIG. 21) to a more horizontal orientation or position or a position wherein axis 164 is perpendicular or angled with respect to axis 106 (FIG. 24). Thus, rod 100 may be advanced through sleeve 50 and installed in a patient utilizing a minimally invasive approach. As described above, in one embodiment stabilization member 16 is rotatably actuatable by insertion device 10 independent of movement along the axis of the sleeve, i.e., the stabilization member 16 may be rotated by insertion device 10 anywhere along the length of the sleeves 22, 24.

A handle 180 may be provided to facilitate insertion of device 10 into sleeves 22, 24. A longitudinal or axial stop may be provided along the exterior of insertion device 10 to ensure that the insertion device and rod attached thereto extends a sufficient length into sleeves 22, 24, such that rod 100 may be positioned sufficiently proximate to anchors 12, 14 attached to the distal ends of sleeves 22, 24.

Figure 25:
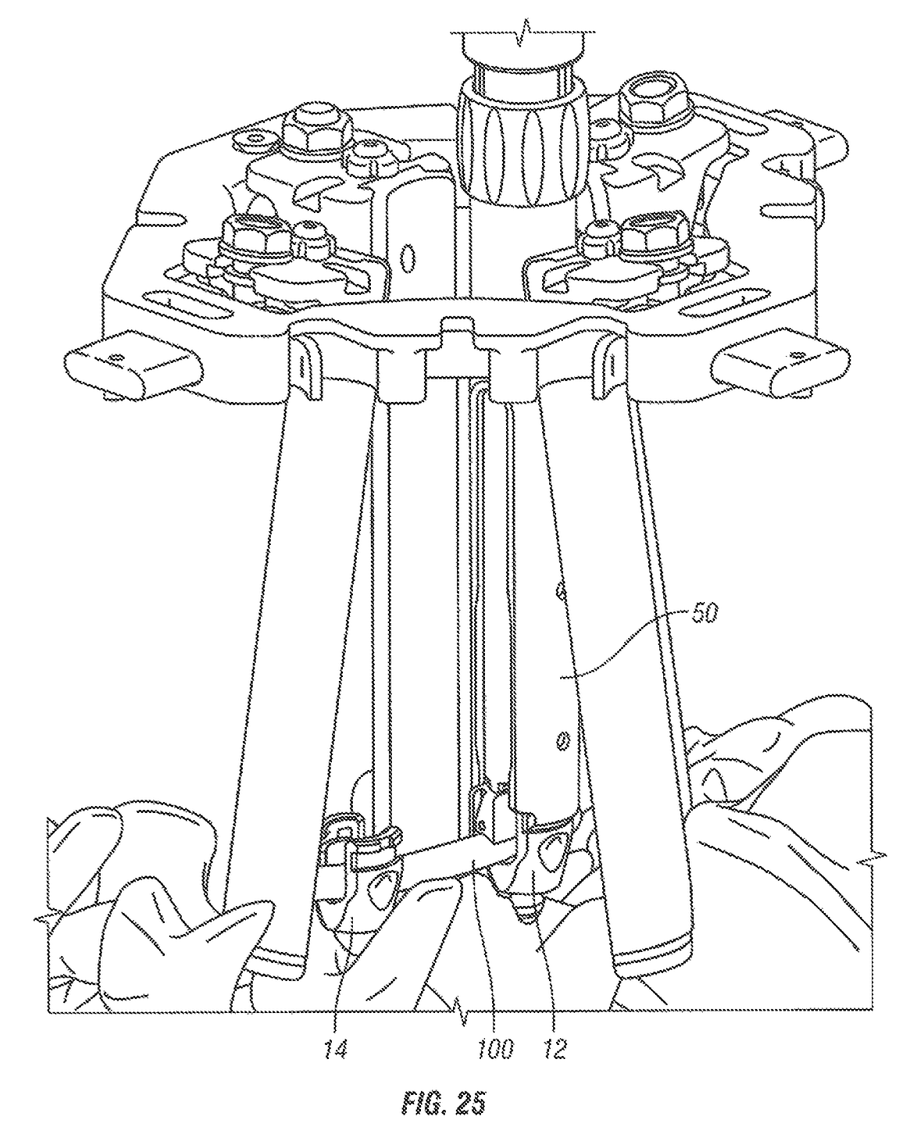
FIG. 25 is a perspective view of another embodiment of a stabilization member and insertion device shown during another embodiment of an installation method according to the present invention.

Surgical techniques or methods using the above described system and device will now be described. According to one embodiment of the present invention, anchors 12, 14 may be implanted into the vertebrae percutaneously, minimally invasively, or through an open or mini-open procedure. In one exemplary embodiment, at least one of the anchors 12, 14 is attached to, mounted on, or retained in sleeve 50, and the sleeve 50 and attached anchor are inserted through an open incision, a tube or cannula, or directly through the skin and tissue of the patient to implant the anchor into bone, such as the pedicles of a vertebrae. In alternate embodiments, anchors 12, 14 can be implanted into bone without a sleeve 50 attached thereto, and sleeve 50 may be mounted on an anchor after it is implanted. For example, as shown in FIG. 25, according to one embodiment, anchors 12, 14, may be installed utilizing a retractor system 190, and one of the anchors 12, 14 may have a sleeve attached thereto while one or more additional anchors does not have a sleeve attached. One exemplary retractor system 190 that may be utilized is disclosed in U.S. patent application Ser. No. 11/422,511, the entire contents of which are incorporated herein by reference. In another exemplary embodiment, shown in FIG. 1, both anchors 12, 14 may have a sleeve attached thereto.

Any imaging system known to those skilled in the art may be utilized to determine and locate optimum placement and orientation of the anchors in the vertebrae and/or to identify locations for entry of the anchors. Other methods known by skilled artisans for locating and placing anchors 12, 14 into the vertebrae may be also used, including, but not limited to, a CT scan or x-ray, any known viewing instrument or apparatus, endoscopic, and microscopic monitoring.

Any known methods of locating and preparing the pedicle for screw implantation may be utilized. In this regard, according to one known minimally invasive technique, after location of the entrance point, instrumentation of the pedicle may begin with the insertion of a cannulated needle through the skin of a patient to the intersection of the facet and transverse process of a vertebral body to which an anchor is to be implanted. A Kirschner wire or guidewire may be inserted through the needle cannula and into the pedicle. Successive dilation cannulas may be subsequently inserted over the guidewire to dilate the fascia and muscle until a working cannula is large enough to accommodate anchor 12 or 14. All but the largest cannula may be removed from the working cannula to expose a passageway through the skin to the pedicle or insertion site. In one embodiment, a hole in the pedicle may be prepared by placing a cannulated drill and/or tap over the guidewire and through the working cannula to prepare the pedicle for screw insertion. In other embodiments, the pedicle may be prepared with other instruments known in the art, including but not limited to an awl, a trocar, and a needle.

Any known methods of installing a pedicle screw into a prepared pedicle may be utilized. In this regard, according to one known minimally invasive technique, a cannulated anchor, such as screw 32 attached to sleeve 50, may be placed over the guidewire and advanced through the working cannula to the prepared pedicle. A driving tool such as a cannulated screw driver may be used to rotate screw 32 and threadedly engage screw 32 to the bone. Sleeve 50 may follow screw 32 to the bone and the screw driver and guidewire may be removed. The working cannula may also subsequently be removed, leaving the sleeve 50 and screw 32 secured to the bone.

Figure 21:
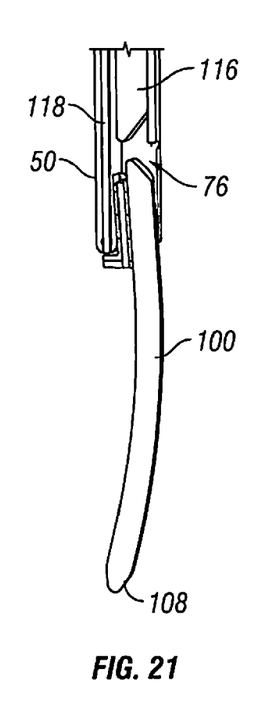
FIG. 21 is a partial cross-sectional view of the insertion device of FIG. 2 shown in a first position.
Figure 22:
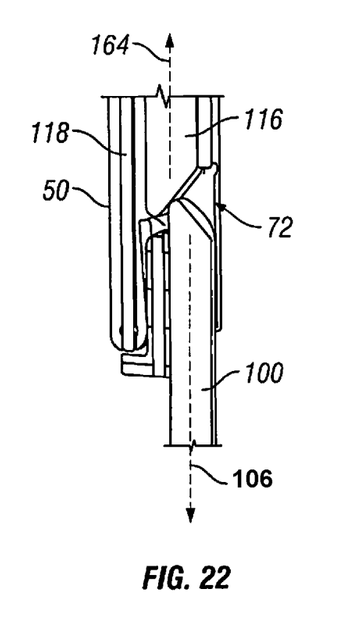
FIGS. 22-24 are partial cross-sectional views of the insertion device of FIG. 2 shown in second, third and fourth positions, respectively.
Figure 23:
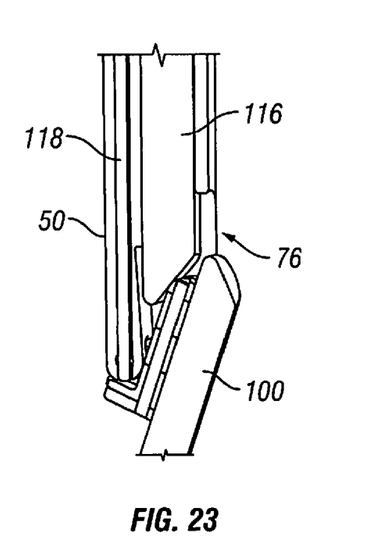

With the anchors 12, 14 secured to the bone and at least one sleeve 50 extending from at least one anchor, stabilization member 16 may be installed between anchors 12, 14 utilizing insertion device 10. In this regard, stabilization member 16 is positioned on insertion device 10 and may be inserted into sleeve 50 with the stabilization member 16 initially in a generally vertical position (as shown in FIGS. 21-22). As insertion device 10 is advanced in the distal direction within sleeve 50 and shaft 116 is moved in the distal direction, rod 100 rotates or pivots about pivot axis 148 to a more horizontal position (as shown in FIG. 24). In this regard, insertion device 10 moves stabilization member 16 in a distal direction toward anchors 12, 14. The proximal end of rod 100 swings outward through opening 76 of sleeve 50 and the distal tip 108 of stabilization member 100 is advanced toward the channels 26 of an adjacent anchor 14. In one exemplary embodiment, as the insertion device 10 is advanced distally into sleeve 50 and shaft 116 is advanced distally with respect to the outer guide tube 118 of insertion device 10, the tip 108 of stabilization member 100 follows a generally elliptical path entering the patient through a first opening and traveling toward the second anchor 14 and through the channel 26 of the second anchor. With rod 100 in a more horizontal position, rod 100 may be then inserted into the channel 26 of the first anchor 12 by advancing the rod insertion tool 10 distally toward the distal end of sleeve 50. According to one variation, the clamp members 110, 112 fit within channel 26 of anchor 12 such that rod 100 may be loaded into the anchor at the same axial location as the clamp members 110, 112 grip or clamp the rod. Sufficient clearance, space or room is also provided within the channel that clamp members may be radially separated apart to release or disengage rod 100 so as to leave rod 100 installed within channel 26

The clamp members 110, 112 may be unclamped from rod 100 to allow the stabilization member 16 to be removed from the insertion device. Once stabilization member 16 is placed within anchors 12, 14 to the desired position, a cap and/or set screw may be driven downward, such as through sleeve 50, to contact stabilization member 16 and fix stabilization member 16 to anchors 12, 14. In this regard, a driving tool may be placed through the central channel of sleeve 50 to tighten the cap and/or set screw against the stabilization member until the stabilization member is firmly seated in coupling element 42 of at least one of anchors 12, 14.

While the invention herein disclosed has been described with reference to specific embodiments and applications thereof, numerous modifications and variations can be made thereto by those skilled in the art without departing from the scope of the invention as set forth in the claims.

What is claimed is:

1. A stabilization member insertion device, comprising:
an outer guide tube extending from a proximal end to a distal end,
first and second clamping members pivotably attached to the distal end,
the first clamping member including a first generally cylindrical protrusion insertable into the distal end of the outer guide tube and the second clamping member including a second generally cylindrical protrusion insertable into the distal end of the outer guide tube,
wherein the first and second clamping members are coupled by a pin extending through a first and second opening in the first and second clamping members, respectively, and
a pin assembly extending through the insertion device, wherein when in a first position, a distal end of the pin assembly is spaced away from the first and second protrusions to allow the first and second clamping members to pivot apart, and when in a second position, the distal end of the pin assembly is positioned between the first and second protrusions to allow the first and second clamping members to move towards one another, thereby configured to hold a stabilization member therebetween.

2. The stabilization member insertion device of claim 1, wherein the outer guide tube has a pusher member extending therethrough, wherein the pusher member is movable with respect to the outer guide tube along a longitudinal axis.

3. The stabilization member insertion device of claim 2, wherein the pusher member is operably connected to a knob such that rotation of the knob causes linear translation of the pusher member with respect to the outer guide tube.

4. The stabilization member insertion device of claim 3, wherein the pusher member is integral to a threaded drive shaft, the knob is internally threaded to mate with external threads of the drive shaft such that rotation of the knob causes the linear translation of the pusher member.

5. The stabilization member insertion device of claim 1, wherein a proximal end of the pin assembly includes a finger portion configured to engage an interior of a thumb nut such that as the thumb nut is rotated, the pin assembly is linearly advanced or retracted.

6. The stabilization member insertion device of claim 1, wherein the first clamping member includes a plurality of first flange portions extending laterally inward and the second clamping member includes a plurality of second flange portions extending laterally inward, wherein the first and second clamping members are assembled with the first and second flange portions overlapping laterally.

7. The stabilization member insertion device of claim 1, wherein the first and second clamping members each define a clamp ridge along a portion of a lower edge of the respective first and second clamping members.

8. The stabilization member insertion device of claim 1, wherein the stabilization member insertion device is operable to place the stabilization member between first and second anchors.

9. A stabilization member insertion device, comprising:
a body extending from a proximal end to a distal end,
first and second clamping members pivotably attached to the distal end,
the first clamping member including a first generally cylindrical protrusion positioned in a first opening in the distal end of the body and the second clamping member including a second generally cylindrical protrusion positioned in a second opening in the distal end of the body,
wherein the first and second clamping members are coupled by a pin extending through a first and second opening in the first and second clamping members, respectively, and
a pin assembly having a first position where a distal end of the pin assembly is spaced away from the first and second protrusions to allow the first and second clamping members to pivot apart, and a second position where the distal end of the pin assembly is positioned between the first and second protrusions to allow the first and second clamping members to move towards one another, thereby configured to hold a stabilization member therebetween.

10. The stabilization member insertion device of claim 9, wherein the body has a pusher member extending therethrough, wherein the pusher member is movable with respect to the body along a longitudinal axis.

11. The stabilization member insertion device of claim 10, wherein the pusher member is operably connected to a knob such that rotation of the knob causes linear translation of the pusher member with respect to the body.

12. The stabilization member insertion device of claim 11, wherein the pusher member is integral to a threaded drive shaft, the knob is internally threaded to mate with external threads of the drive shaft such that rotation of the knob causes the linear translation of the pusher member.

13. The stabilization member insertion device of claim 9, wherein a proximal end of the pin assembly includes a finger portion configured to engage an interior of a thumb nut such that as the thumb nut is rotated, the pin assembly is linearly advanced or retracted.

14. The stabilization member insertion device of claim 9, wherein the first clamping member includes a plurality of first flange portions extending laterally inward and the second clamping member includes a plurality of second flange portions extending laterally inward, wherein the first and second clamping members are assembled with the first and second flange portions overlapping laterally.

15. The stabilization member insertion device of claim 9, wherein the first and second clamping members each define a clamp ridge along a portion of a lower edge of the respective first and second clamping members.

16. The stabilization member insertion device of claim 9, wherein the stabilization member insertion device is operable to place the stabilization member between first and second anchors.

17. A stabilization member insertion device, comprising:
an outer guide tube extending from a proximal end to a distal end,
first and second clamping members pivotably attached to the distal end, the first and second clamping members having first and second protrusions, respectively, extending inwardly from a sidewall of each clamping member, respectively,
wherein the first and second clamping members are coupled by a pin extending through a first and second opening in the first and second clamping members, respectively, and
a pin assembly extending through the outer guide tube, wherein when in a first position, a distal end of the pin assembly is spaced away from the first and second protrusions to allow the first and second clamping members to pivot apart, and when in a second position, the distal end of the pin assembly is positioned between the first and second protrusions to allow the first and second clamping members to move towards one another, thereby configured to hold a stabilization member therebetween.

18. The stabilization member insertion device of claim 17, wherein the outer guide tube has a pusher member extending therethrough, wherein the pusher member is movable with respect to the outer guide tube along a longitudinal axis.

19. The stabilization member insertion device of claim 18, wherein the pusher member is operably connected to a knob such that rotation of the knob causes linear translation of the pusher member with respect to the outer guide tube.

20. The stabilization member insertion device of claim 17, wherein a proximal end of the pin assembly includes a finger portion configured to engage an interior of a thumb nut such that as the thumb nut is rotated, the pin assembly is linearly advanced or retracted.

* * * * *